United States Patent
McKinnon

(10) Patent No.: US 7,947,018 B2
(45) Date of Patent: May 24, 2011

(54) ROTATIONALLY ACTIVATED BLOOD CONTROL

(75) Inventor: Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/114,886

(22) Filed: May 5, 2008

(65) Prior Publication Data
US 2009/0275901 A1   Nov. 5, 2009

(51) Int. Cl.
*A61M 5/178*   (2006.01)

(52) U.S. Cl. ......... 604/167.03; 604/167.01; 604/167.02; 604/256; 604/167.04; 604/200; 604/201; 604/246; 604/248

(58) Field of Classification Search ............. 604/164.01, 604/244, 246, 248, 256, 167.02–167.06, 604/846–847, 201, 247; 137/493, 846–847
See application file for complete search history.

(56) References Cited

U.S. PATENT DOCUMENTS

| | | | |
|---|---|---|---|
| 969,573 A * | 9/1910 | Storrs ............................ 239/546 |
| 3,965,925 A | 6/1976 | Gooch | |
| 3,977,400 A | 8/1976 | Moorehead | |
| 4,133,457 A * | 1/1979 | Klassen ......................... 222/212 |
| 4,842,591 A * | 6/1989 | Luther ........................... 604/537 |
| 5,330,437 A * | 7/1994 | Durman .................... 604/167.04 |
| 5,370,624 A * | 12/1994 | Edwards et al. .......... 604/167.05 |
| 6,050,978 A * | 4/2000 | Orr et al. ....................... 604/249 |
| 6,228,060 B1 * | 5/2001 | Howell .................... 604/167.04 |
| 6,533,759 B1 * | 3/2003 | Watson et al. ........... 604/167.02 |
| 2002/0062106 A1 * | 5/2002 | Chu et al. ................ 604/167.01 |
| 2003/0195472 A1 * | 10/2003 | Green et al. ............. 604/167.04 |
| 2005/0049555 A1 * | 3/2005 | Moorehead et al. .......... 604/122 |
| 2005/0113757 A1 * | 5/2005 | McFarlane ............... 604/167.03 |
| 2007/0106228 A1 | 5/2007 | Bell et al. | |

FOREIGN PATENT DOCUMENTS

EP          1 197 241 A1    4/2002

* cited by examiner

*Primary Examiner* — Theodore J Stigell
*Assistant Examiner* — Edelmira Bosques
(74) *Attorney, Agent, or Firm* — Craig Metcalf; Mony Ghose; Kirton & McConkie

(57) ABSTRACT

A medical device having a vascular access device including a rotationally activated flow control valve having, a body including a distal adapter and a proximal adapter defining a lumen extending therethrough and a septum. A method of use in which the connection of first and second medical devices results in the automatic activation of the rotational flow control valve.

17 Claims, 10 Drawing Sheets

ROTATIONALLY ACTIVATED BLOOD CONTROL

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

Although several techniques for placing such catheters are practiced in the art, many generally include the step of inserting at least a portion of the needle into the target vessel and then sliding the catheter over the needle into place. The medical worker attempts to verify proper placement of the catheter within the blood vessel. Catheter and introducer needle assemblies have been provided that include means for verifying proper placement of the catheter in a blood vessel such as a flashback chamber in the catheter hub or a notch in the introducer needle.

Once placement of the needle has been confirmed by the observation of flash, the user may temporarily occlude flow in the blood vessel at the catheter tip, remove the needle, leaving the catheter in place, and attach a device to the catheter for fluid removal, input, or to seal the catheter. This process has been somewhat difficult in practice since many placement sites simply do not allow easy occlusion of the target vessel. Additionally, even when such occlusion is achieved, it may be imperfect, thus resulting in blood leaking from the catheter, endangering the medical personnel employing it.

Catheter and introducer needle assemblies have thus been provided in the art that provide a variety of seals or "septa" for preventing outflow of fluid during and following removal of the introducer needle. These structures are generally elastomeric plates designed to closely conform to the shape of a needle during storage and use to prevent leaking, then to seal upon removal of the needle. In an ideal vascular access device, the septum would continuously seal the patient's vascular system, which may include external vascular equipment intentionally coupled to the patient's internal vascular system by a medical practitioner, from the external environment.

As with most systems, one of the biggest challenges to the proper function of the vascular access device is when there is a change in the system, such as when different medical devices are connected or disconnected from the vascular access device. If the seal against the external environment is broken during the connection or disconnection of a medical device, there is the possibility of infection being introduced into the patient's vascular system. Additionally, if a pressure difference is created across the vascular access device, there becomes the possibility that blood will be drawn up the catheter system and possibly into the vascular access device or beyond. Alternatively, a pressure difference across the vascular access device may make it more difficult to couple other medical devices to the vascular access device.

Vascular access devices are often coupled with a blunted cannula, such as the tip of a syringe, with a male Luer connector, or with other medical devices. These medical devices may be coupled to the vascular access devices by pressing a portion of the medical device into a slit or passage in the septum. The tip penetrates the device deforming and separating at least portions of the two opposing slit surfaces of the septum. The septum and the slit may be configured to seal, or at least substantially seal, around the tip as it is inserted into the vascular access device. Accordingly, the surfaces near the slit ends may not be separated until the tip is sufficiently inserted into vascular access device. The tip serves to open the slit to allow fluid to pass through the device, into the catheter, and out the end of the catheter when the device is in use.

Repeated transitions of the septum between open and closed configurations apply stress to the septum. In some experiences the septum has been seen to tear, either slightly or more significantly, at the edges of the slit that allows other devices to access the internal vascular system through the lumen of the body. In previous vascular access devices, two common tear patterns have been observed: radial tearing and circumferential tearing. Depending on the nature of the tear, the impacts of the tear may include a decrease in the quality of the seal formed by the septum or pieces or particles of the septum breaking free from the remainder of the septum.

Some medical devices are coupled to the vascular access device through a twisting motion by which the body or other portion of the medical device is coupled to the body of the vascular access device and by which a portion of the medical device is disposed in the slit or passage of the septum. Other methods of coupling the vascular access device to one or more medical devices may be used as well.

Therefore the need exists for a more efficient method of valving in vascular access devices which allows for the valve to open and close automatically and provides a minimal fluid flow restriction hence better flush properties, with a low stress imparted on the septum.

BRIEF SUMMARY OF THE INVENTION

According to one aspect, a medical device is provided having a vascular access device including a rotationally activated flow control valve. Various rotational mechanisms can be used; one embodiment includes a body including having at least two body sections such as for example a distal adapter and a proximal adapter defining a lumen extending therethrough and a septum. The septum at least substantially seals the lumen extending through the body, wherein rotation of one of the proximal adapter or the distal adapter in relation to the other results in the activation of the valve.

According to another aspect, a method is provided, including providing a first medical device having a lumen and rotationally activated valve, connecting a second medical device having a lumen to the first medical device such that the rotationally activated valve is automatically opened and both lumen are in fluid communication. The plane of rotation may be substantially perpendicular to said lumen. The method may also include disconnecting the second medical device from the first medical device such that the rotationally activated valve is automatically closed.

These and other features and advantages of the present disclosure may be incorporated into vascular access devices and will become more fully apparent from the following description and appended claims, or may be learned by the practice and implementation of the present disclosure. As described above, the present disclosure does not require that all of the features described herein be incorporated into every embodiment nor is it required that certain features be used exclusive of other features. Vascular access devices within the scope of the present disclosure may include one or more combinations of the features described herein.

DETAILED DESCRIPTION OF THE INVENTION

It will be readily understood that the components of the present disclosure, as generally described and illustrated in the figures herein, could be arranged and designed in a wide variety of different configurations. Thus, the following more detailed description, as represented in the figures, is not intended to limit the scope of the disclosure, but is merely a representative of exemplary combinations of the components.

The term "proximal" is used to denote a portion of a device which, during normal use, is nearest the user and furthest from the patient. The term "distal" is used to denote a portion of a device which, during normal use, is farthest from the user wielding the device and closest to the patient. The term "activation" of a valve is used to denote the action of opening or closing of such a valve, a rotational activation therefore requires a rotational or twisting force to activate i.e. open or close the valve. The term "automatic" activation of a valve is used to denote the activation of a valve without the need of a separate dedicated activation step, e.g. by connecting a medical device to the automatically activated valve.

Figure 1:
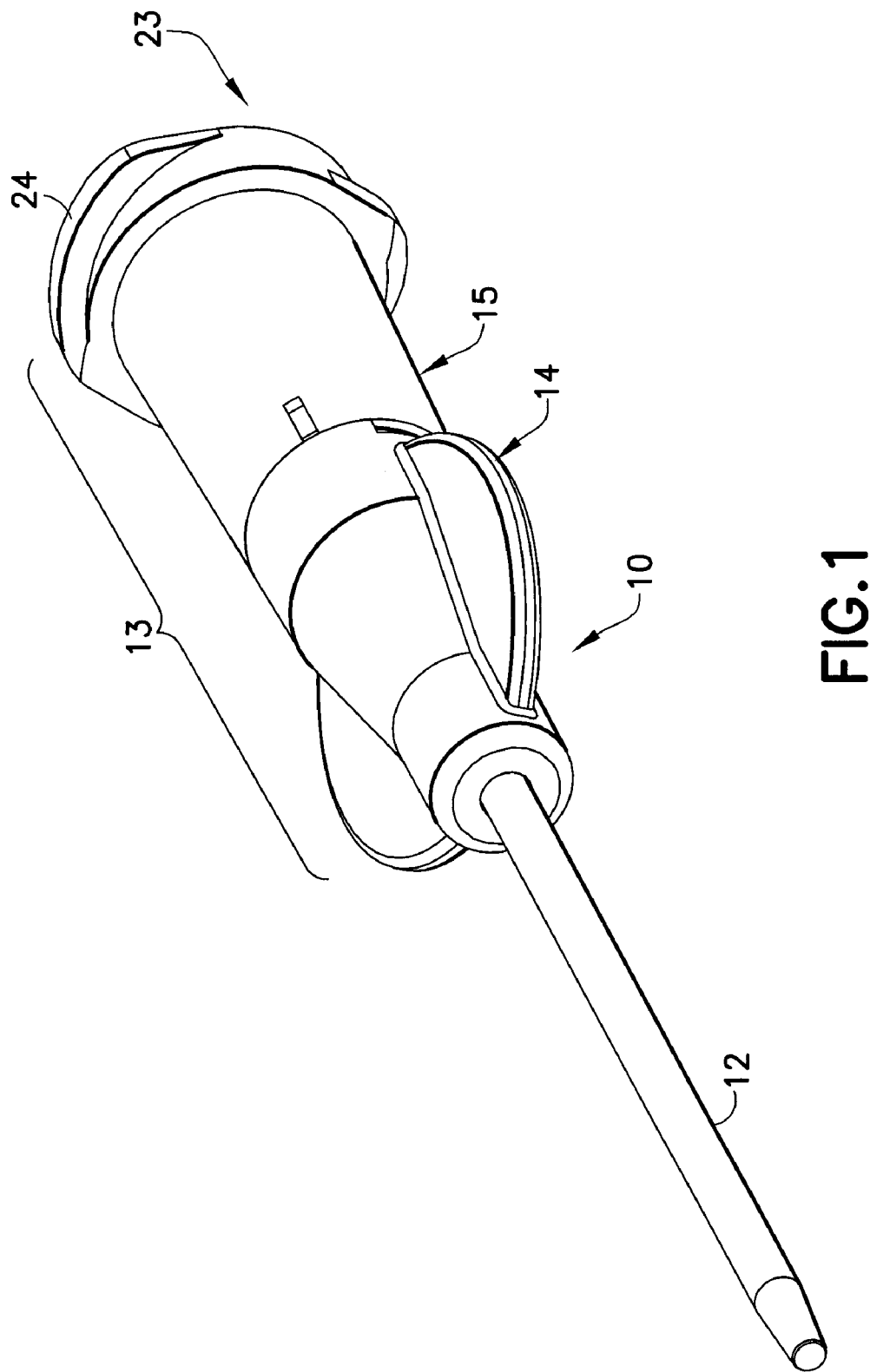
FIG. 1 is a perspective view of a medical device including a vascular access device having a rotational activation flow control valve in accordance with an embodiment of the subject invention.
Figure 2:
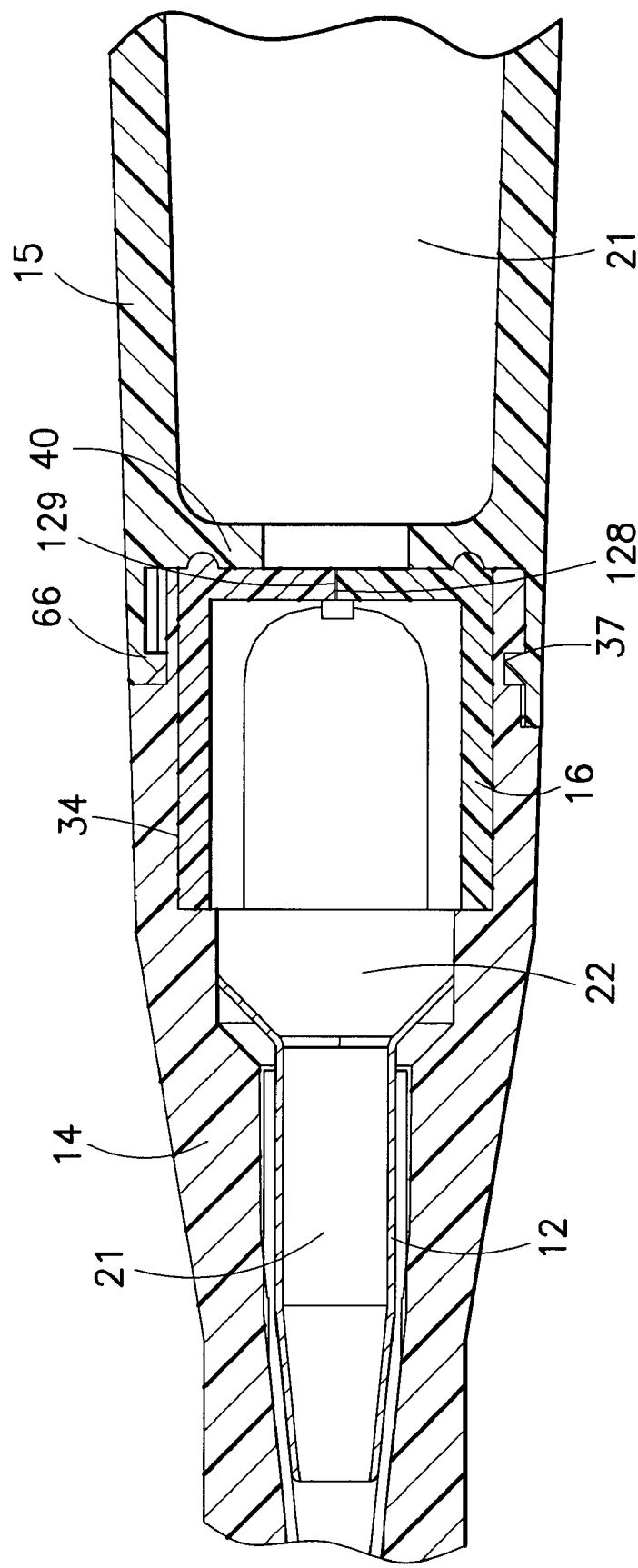
FIG. 2 is a cross section view of the rotational activation flow control valve as shown in FIG. 1.

A device comprising a rotational activation flow control valve in accordance with an embodiment of the subject invention is illustrated in FIGS. 1 to 11. Referring now to FIGS. 1 and 2 a vascular access device 10 is used to introduce a substance via a catheter 12 across the skin and into a blood vessel of a patient. The vascular access device 10 includes a body 13 with a lumen 21 and a septum 16 placed within the lumen 21. The vascular access device 10, including the body 13 and the septum 16, will be more thoroughly described with reference to the remaining figures where particular features are better illustrated.

As shown in FIG. 2, Body 13 includes a distal adapter 14, a proximal adapter 15 and a septum 16 which form a rotational activation flow control valve in accordance with an embodiment of the subject invention. Septum 16 is housed within distal adapter 14 and forms a seal with proximal adapter 15 to prevent leakage of fluid from the proximal end of the body when the valve is in the closed position. Distal adapter 14 is connected to proximal adapter 15 in such a way that proximal adapter 15 can be rotated independently in relation to distal adapter 14.

Body 13 may also include connection regions 23, such as female luer lock connector 24 or a male luer lock connector (not shown), to enable the vascular access device to be selectively coupled to other medical devices. Additionally, the body 13 may include grips 26, which may be wings or other structures on the surface of the body 13, to facilitate the manipulation of the vascular access device 10. The body 13 may include other features or structures common to vascular access devices.

Figure 3:
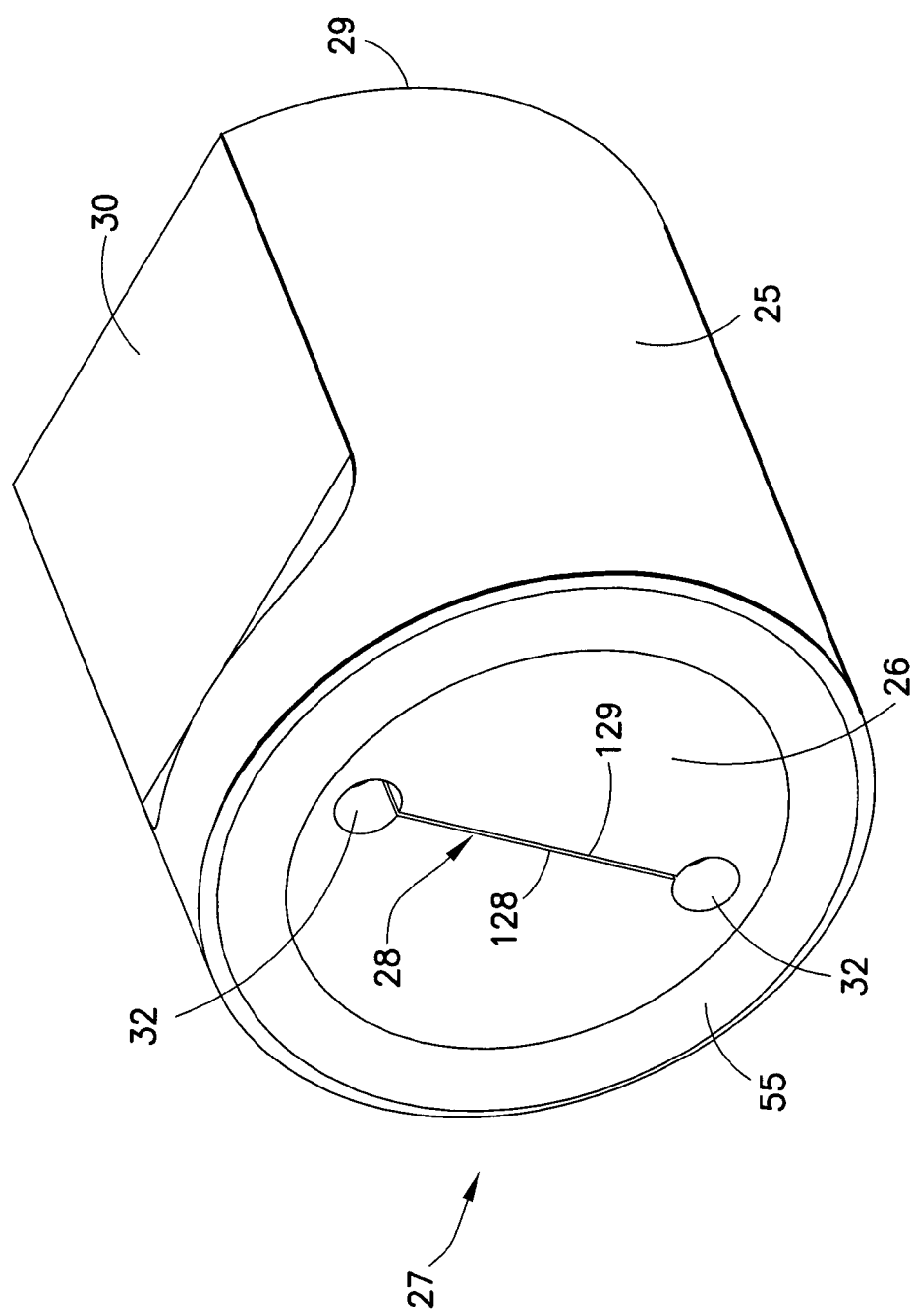
FIG. 3 is a perspective view of a septum of the rotational activation flow control valve as shown in FIG. 1.
Figure 4:
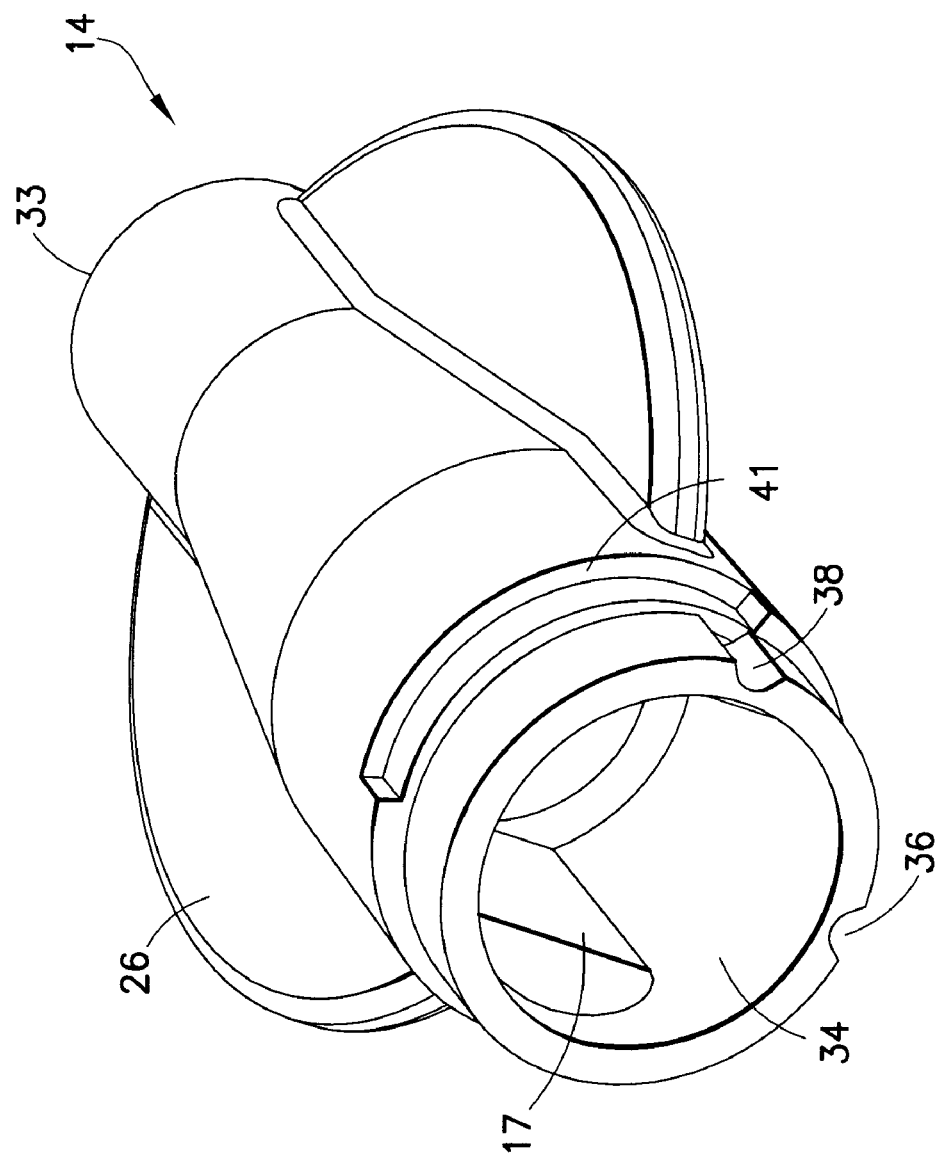
FIG. 4 is a perspective view of the proximal end of a distal adapter of the rotational activation flow control valve as shown in FIG. 1.
Figure 5:
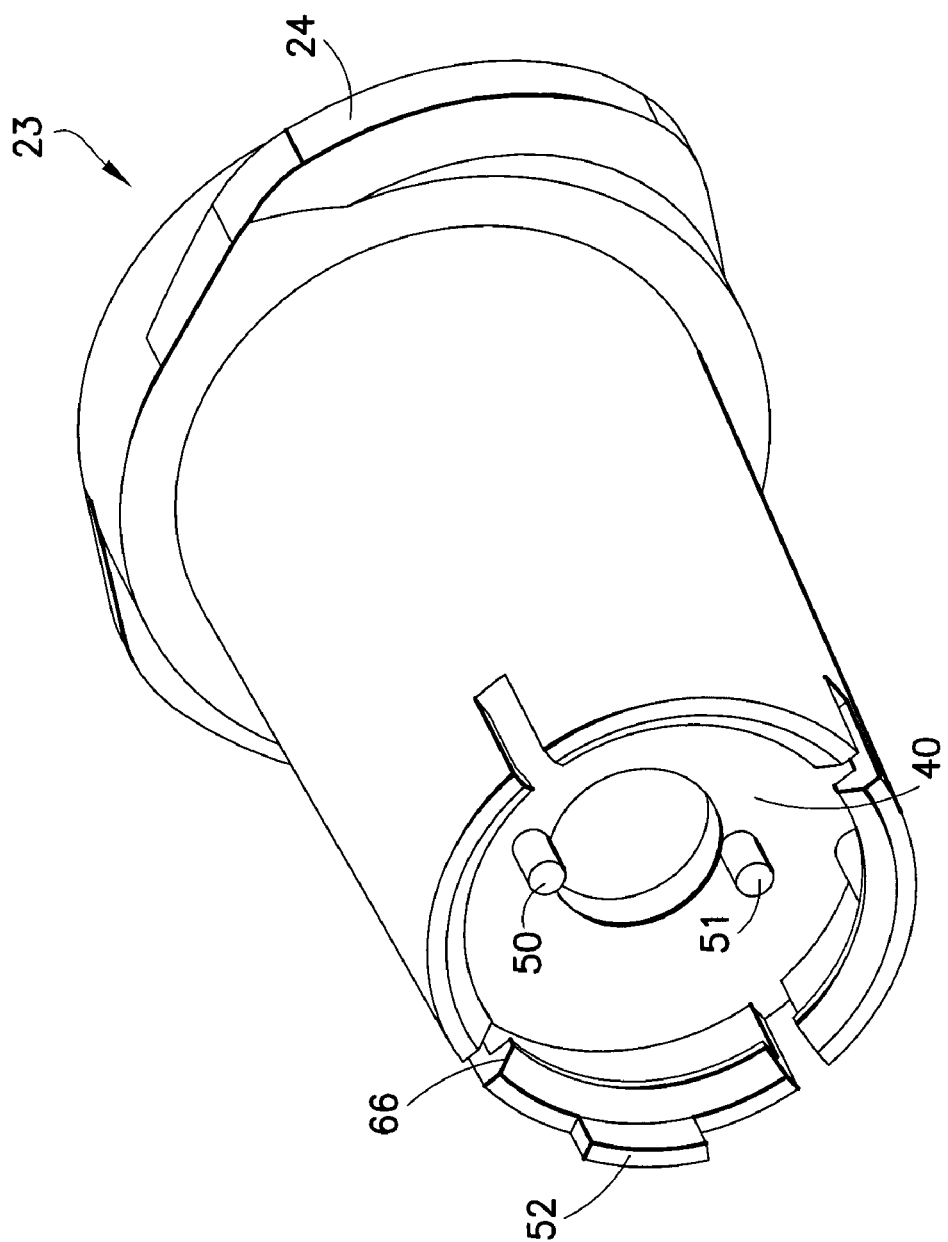
FIG. 5 is a perspective view of the distal end of a proximal adapter of the rotational activation flow control valve as shown in FIG. 1 as seen.

FIG. 3 shows a septum 16 including a cylinder 25 having a distal end 29 and a disk 26 located at the proximal end 27. Two flat portions 30 are present on the outer surface of cylinder 25. Septum 16 further includes two holes 31, 32 which are connected by a slit 28, extending through disk 26 having opposing slit surfaces 128, 129. The opposing slit surfaces 128, 129 of the slit 28 are designed to closely conform to the shape of an introducer needle during storage and prevent an outflow of fluid during and following removal of the introducer needle, then to seal upon removal of the introducer needle. In addition the opposing slit surfaces 128, 129 may be moved apart to open the slit 28, e.g. when the tip of a blunt cannula of a medical device is inserted into a vascular access device 10. Disk 26 also has a circular sealing bead 55 on the proximal surface towards the outer circumference of disk 26.

With continuing reference to FIGS. 2-5, in this embodiment, Septum 16 is substantially disposed within distal adapter 14 within septum housing 34. A fluid seal is formed between septum 16 and proximal adapter 15 by the compression of sealing bead 55 against the distal face of annular wall 40 to prevent fluid leakage past septum 16 when the valve is closed. Two posts 50, 51 which project from the distal face of annular wall 40 are received in the two holes 31, 32 in disk 26. Proximal adapter 15 is connected to distal adapter 14 via a snap fit engagement between snap ring 66 on the distal end of proximal adapter 15 and groove 37 on the outer surface of the distal adapter 14. This snap fit engagement allows proximal adapter 15 to rotate in relation to distal adapter 14. Rotation of the proximal adapter in a plane that is substantially perpendicular to the lumen 21 of proximal adapter 15 causes posts 50, 51 to deform slit 28 of septum 16 hence opening the valve through which a separate extravascular device (not shown), such as an IV administration set, may introduce a substance into the vascular access device 10. An IV administration set is one exemplary separate device. Other suitable extravascular devices may include additional vascular access devices, syringes, or other common or yet to be developed medical devices.

At least one retention system may be used each of the various embodiments of the valve to retain the valve in an open or closed position and/or to limit the degree of rotation of one body section in relation to the other body section(s) such that a specified degree of rotation such as 15, 30, 45, 60, 90, 120, 180, 270 or 355 degrees for example will cause the valve to open or close.

Figure 6:
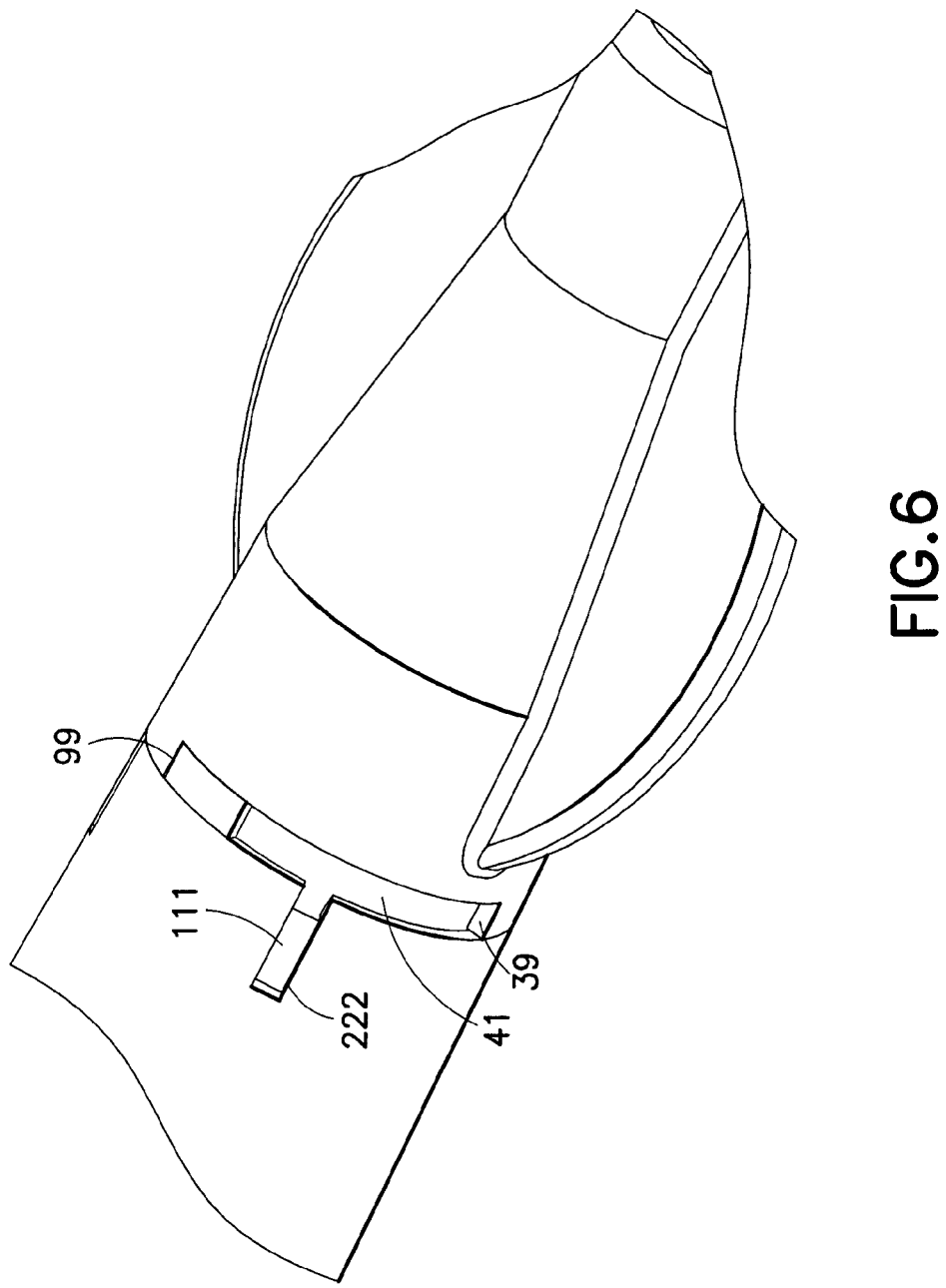
FIG. 6 is a perspective view of a rotation retention mechanism of the valve in accordance with an embodiment of the subject invention with the valve in the closed position.
Figure 7:
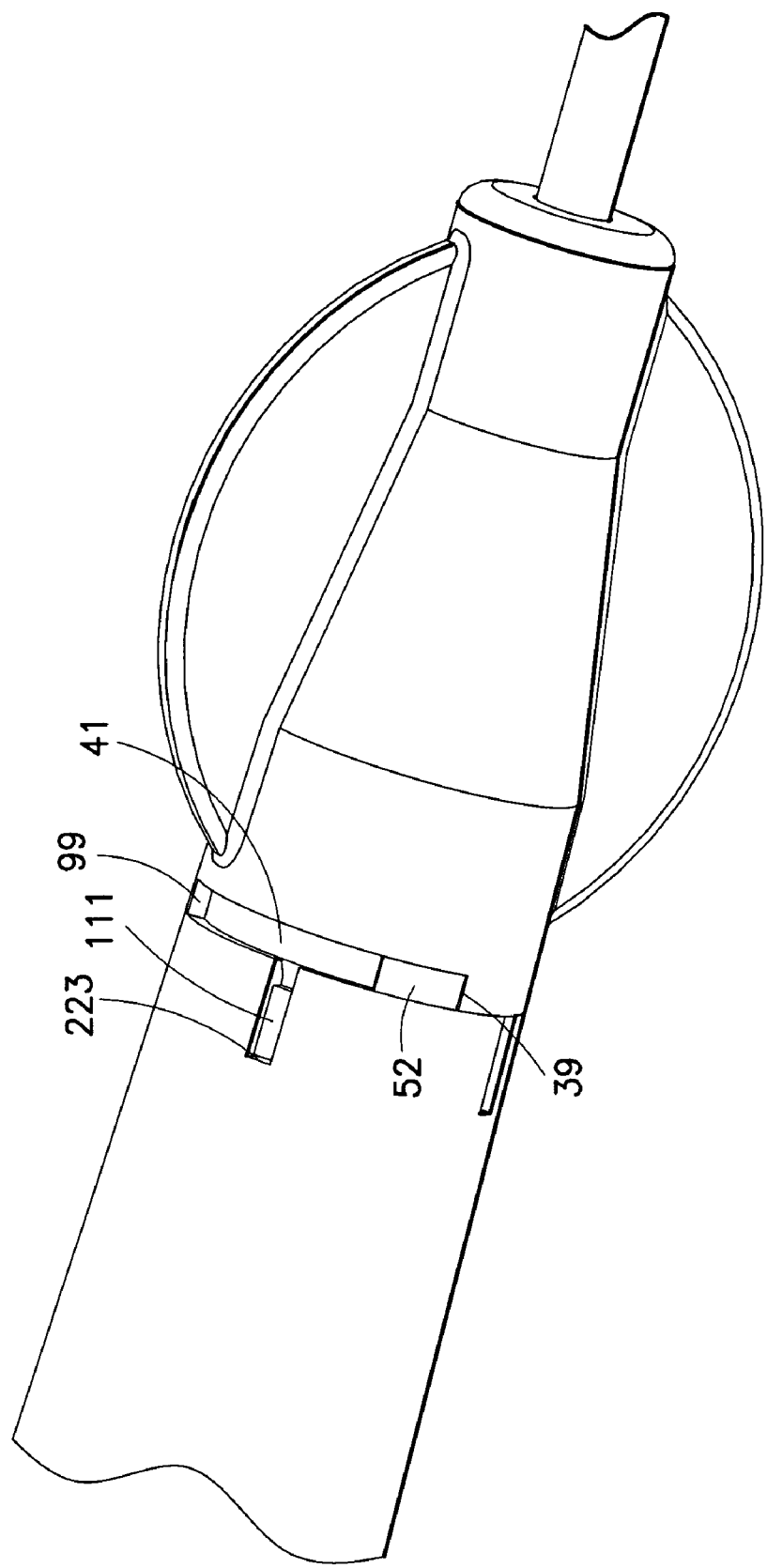
FIG. 7 is a perspective view of the rotation retention mechanism shown in FIG. 6 with the valve in the open position.
Figure 8:
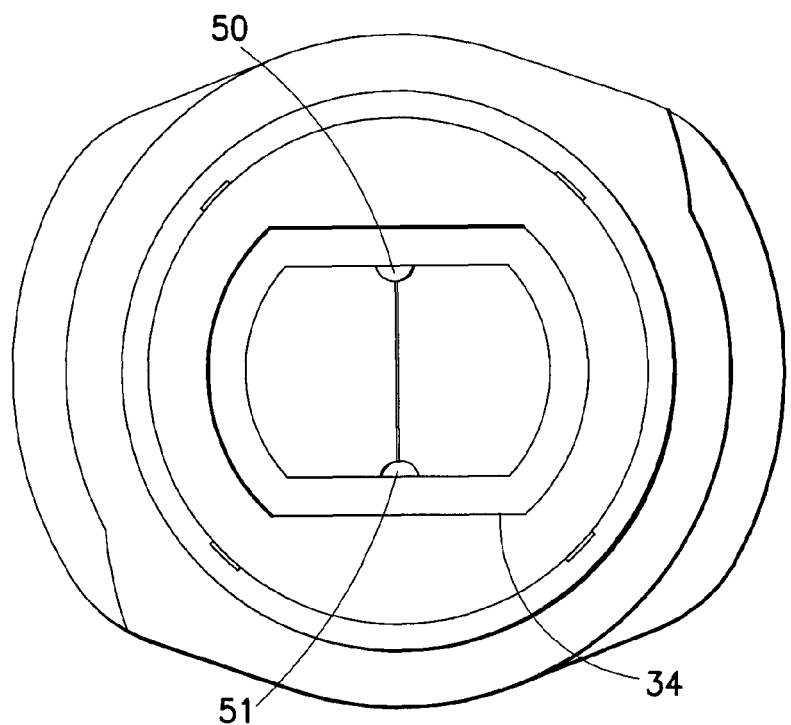
FIG. 8 is an end view of the lumen and septum from the distal end of the distal adapter of the valve with the valve in the closed position.
Figure 9:
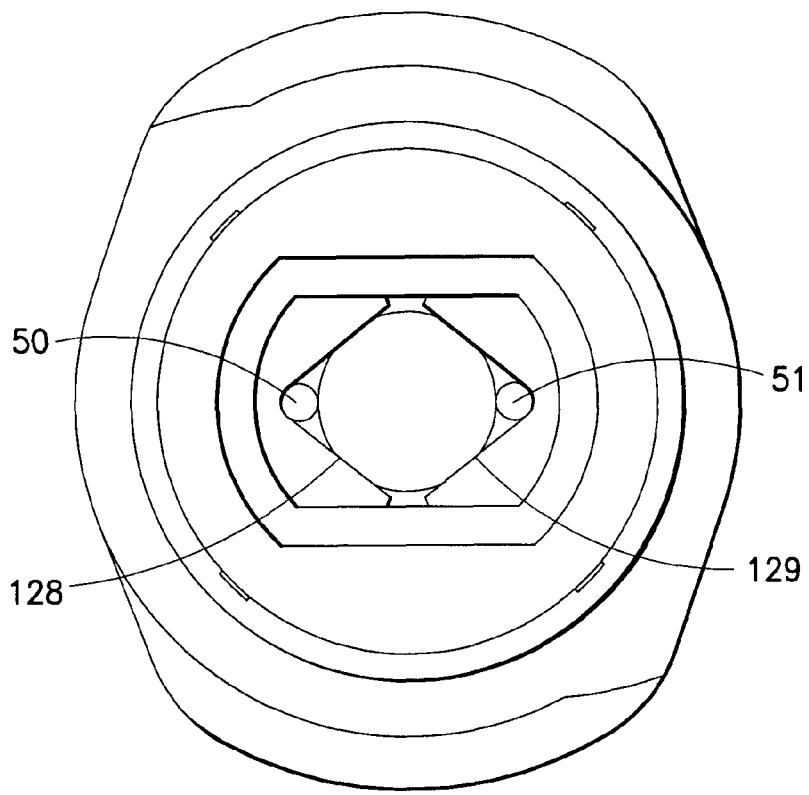
FIG. 9 is an end view of the lumen and septum from the distal end of the distal adapter of the valve with the valve in the open position.
Figure 10:
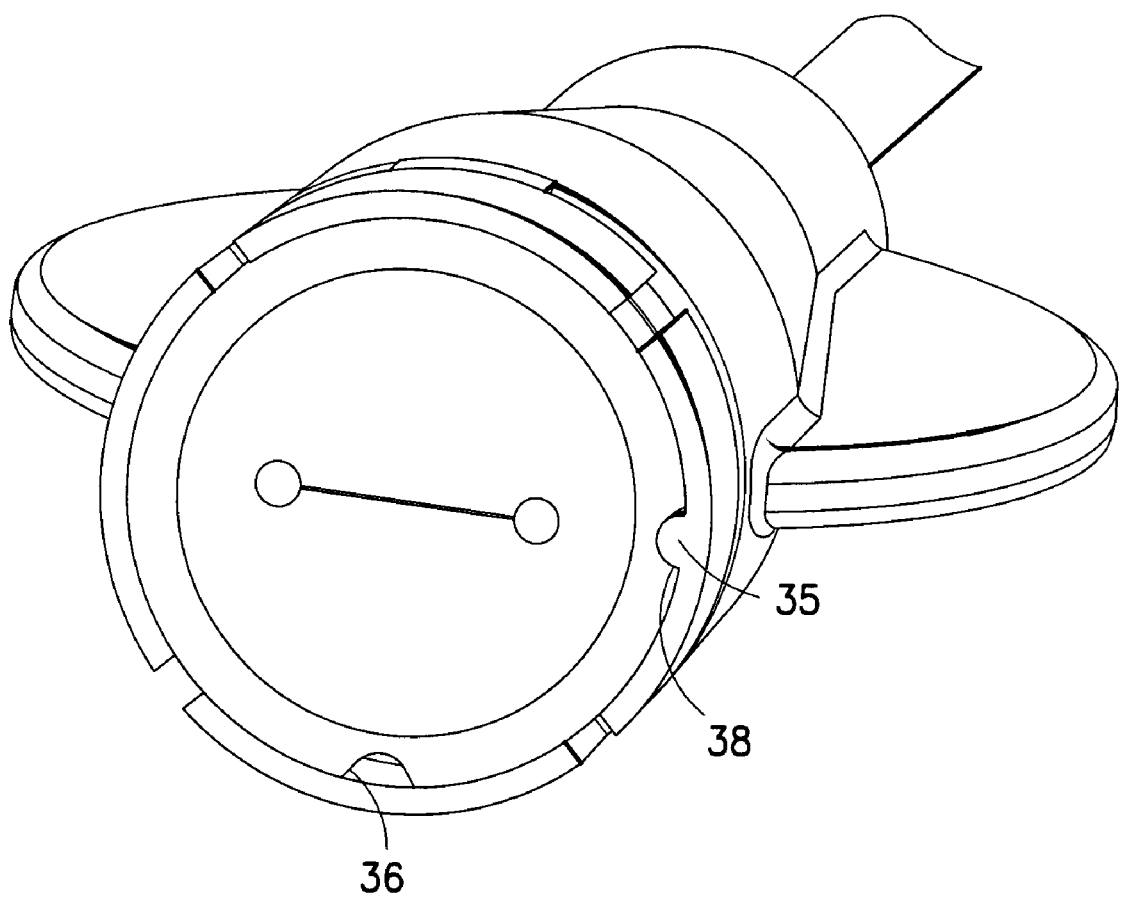
FIG. 10 is a section view of a rotation retention mechanism of the valve in accordance with an embodiment of the subject invention with the valve in the closed position.
Figure 11:
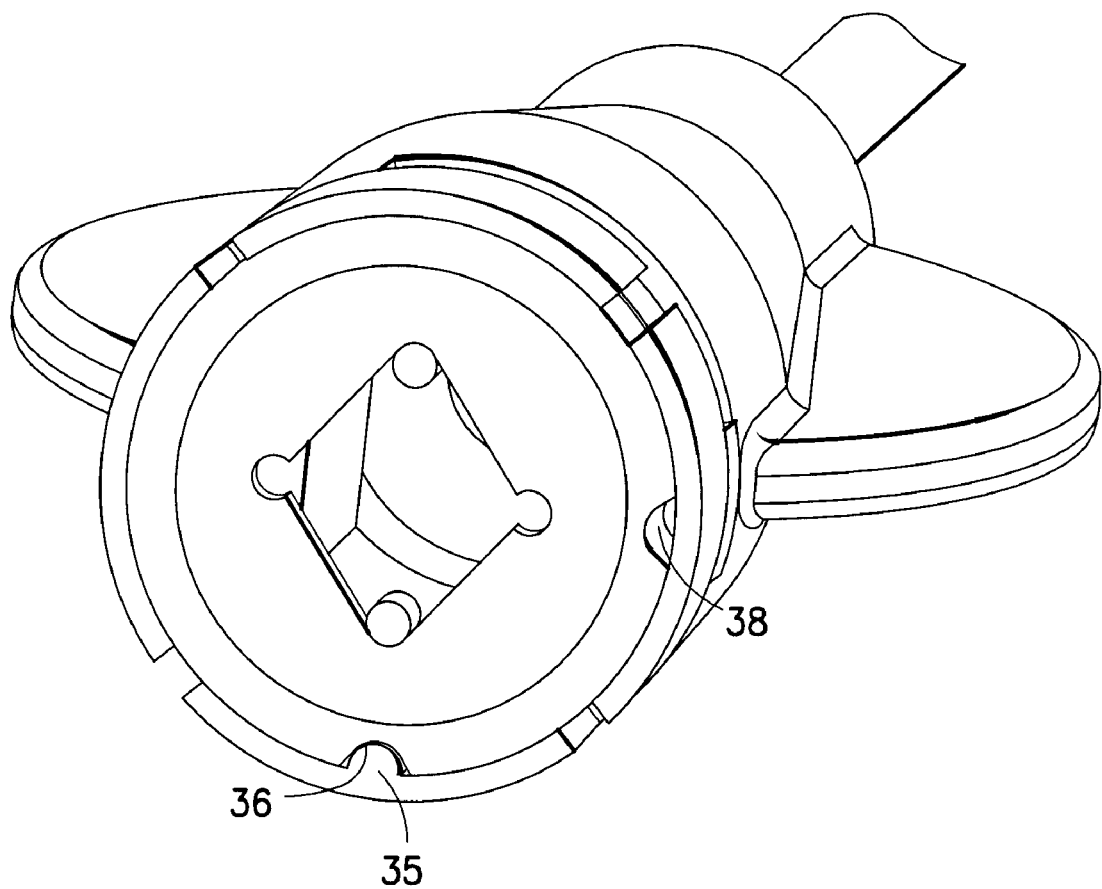
FIG. 11 is a section view of a rotation retention mechanism of the valve in accordance with an embodiment of the subject invention with the valve in the open position.

In the embodiment shown in FIGS. 1 to 11 the valve is retained in the closed or open position and the degree of rotation limited to 90 degrees by the combination of three retention systems, the first being the interaction of a tab 52 on the proximal adapter and a rotation locker 39 on the outer surface of distal adapter (as shown in FIGS. 6 and 7) and the second being the interaction of detent grooves 36 and 38 on the proximal end of distal adapter 14 and detent bump 35 on the inner surface of the distal end of proximal adapter 15 (as shown in FIGS. 10 and 11) and the third being the interaction between key 111 on the outer surface of the distal adapter 14 and snap relief cuts 222 and 223 of proximal adapter 15 (as shown in FIGS. 6 and 7). Thus this embodiment of the valve uses the first 90 degrees of rotation to automatically open or close the valve when connected to the vascular access device.

FIGS. 6, 8 and 10 illustrate this embodiment of the valve in the closed position, in which the septum 16 seals the lumen 21 preventing the flow of any fluid out of the proximal end of body 13. Detent bump 35 is retained in the closed position groove 38 and Tab 52 is retained in the closed position by shoulder 99 and the location of key 111 on the outer surface of the distal adapter 14 in snap relief cut 222 of proximal adapter 15. Therefore a rotational force is required to move the valve from the closed position to open position, thus reducing the possibility of an inadvertent opening of the valve. Sufficient rotational force causes detent bump 35 to be dislocated from closed position groove 38 and depresses key 111 out of snap relief cut 222. Proximal adapter is then rotated in relation to distal adapter 14 with Tab 52 traveling around track 41 until the open position is reached.

FIGS. 7, 9 and 11 illustrate this embodiment of the valve in the open position. The maximum valve aperture occurs when the degree of rotation reaches 90 degrees; hence the open position is limited to 90 degrees from the closed position. This design of valve allows for a smaller flow restriction in the open position when compared to the penetration of a blunt cannula through a split septum, which may provide desirable flow and flush properties within the body of the vascular access device. The rotation of the proximal adapter is limited by contact of tab 52 with rotation locker 39 at the open position; the valve is retained in the open position by the location of detent bump 35 into open position groove 36 and the insertion of key 111 into snap relief cut 223. In this embodiment the amount of rotational force required to open and close the valve are similar, however the valve retention systems can be designed such that a greater force may be required to open or to close the valve. The rotation of the proximal adapter also results in the rotation of posts 50 and 51. The flat portions 30 of septum 16 mates with the internal flat sections 17 of septum housing 34 to inhibit septum 16 from rotating when located in the septum housing 34. Thus posts 50 and 51 rotate, moving out of holes 31, 32 in disk 26 to deform slit 28 by moving apart slit surfaces 128, 129 thereby allowing fluid flow along lumen 21 in body 13.

Automatic activation of the valve in this embodiment can occur when another medical device having a male luer interlok is connected to the vascular access device by female luer lok connector 24. The device can be designed such that the rotational and/or twisting engagement of the male and female threads of the luer interlok provides the rotational force required to overcome the retention mechanisms, rotating the proximal adapter thereby opening the valve. The valve and luer interlok can be designed to allow activation or valve movement to begin on first engagement between the luer threads such that the activation of the valve occurs in parallel with the completion of the luer connection or valve activation can occur subsequent the completion of the threaded luer connection. When disconnecting the second medical device, the valve can also close in parallel with the disconnection or prior to the disconnection movement. The connection region 23 of body 13 and the other medical device can use any suitable complimentary connection engineering or technology such as a threaded connection, a luer lok or any other mating technology which requires or can use a rotational and/or twisting force to complete or disconnect the connection.

Various other designs of rotational mechanisms can be used in which the body of the valve may comprise more than two sections or the body sections may be arranged concentrically as opposed to a longitudinal distal/proximal arrangement.

The body 13 and the septum 16 may be constructed of a variety of suitable materials. Commonly, the body 13 of the vascular access device 10 will be made of a plastic, and preferably a plastic material such as a thermoplastic material that facilitates molding the body. Other methods and materials may be used for manufacturing the body 13, some of which may be currently practiced and some of which may be developed in the future.

Similarly, the septum 16 may be made of a variety of suitable materials and through a variety of suitable manufacturing methods. For example, the septum may be formed from liquid silicone rubber through suitable molding procedures, such as insert molding, injection molding, other molding techniques, or a combination of molding techniques. The septum 16 may also be formed of any dimension capable of providing a slit 28 that, alone or in combination with other features, allows the slit to be deformed but resists tearing when opened. The septum 16, or any septum described herein, may also include a coating of antimicrobial substance on any of its surfaces, especially those surfaces which have contact with fluid.

Although illustrative embodiments of the present invention have been described herein with reference to the examples, it is to be understood that the invention is not limited to those precise embodiments, and that various other changes and modifications may be effected therein by one skilled in the art without departing from the scope or spirit of the invention.

The invention claimed is:

1. A rotationally activated flow control valve comprising,
a body including a distal adapter and a proximal adapter defining a lumen extending therethrough;
a septum interposedly positioned between said distal adapter and said proximal adapter, said septum having a slit extending through said septum, said slit having two opposing slit surfaces, a contact portion of each of said two opposing slit surfaces being in contact when the septum is in a closed position, wherein said septum at least substantially seals said lumen, said septum further comprising at least two holes; and
at least two posts coupled to at least one of said proximal adapter and said distal adapter, wherein said two posts are mated with said holes when said valve is in the closed position, wherein rotation of one of said proximal adapter or said distal adapter in relation to the other repositions said posts within said opening which results in the activation of said valve.

2. The medical device of claim 1, wherein the plane of rotation is substantially perpendicular to said lumen.

3. The medical device of claim 1, wherein said rotation of said proximal adapter in relation to said distal adapter opens or closes said opening of said septum.

4. The medical device of claim 1, wherein a rotation of 90 degrees of one of said adapters in relation to said other adapter is required to fully activate said valve.

5. The medical device of claim 1, wherein the connection of a second medical device to said body causes the rotation of one of said proximal adapter or said distal adapter.

6. The medical device of claim 1, wherein said valve further comprises an interlok for receiving a second medical device, wherein upon rotationally coupling said second medical device to said interlok, said posts of said flow control valve are rotationally repositioned within said opening of said septum thereby activating said valve.

7. The medical device of claim 1, wherein said septum is housed within said distal adapter and forms a fluid seal with said proximal adapter when said valve is in the closed position.

8. The medical device of claim 7, wherein said septum further comprises a flat disc and sealing bead located on a proximal face of said disc.

9. The medical device of claim 8, wherein said sealing bead and said flat disc forms said fluid seal with said proximal adapter when said valve is in the closed position.

10. The medical device of claim 1, wherein rotation of said proximal adapter removes said posts from said holes which results in said posts deforming said opening to open said valve.

11. The medical device of claim 1, wherein the connection of a second medical device to said body causes said valve to open.

12. The medical device of claim 11, wherein disconnection of said second medical device from said body causes said valve to close.

13. The medical device of claim 1, wherein said vascular access device is a catheter.

14. The medical device of claim 1, wherein said proximal adapter further comprises a connection region to enable said vascular access device to be selectively coupled to other medical devices.

15. A medical device comprising:
    a rotationally activated flow control valve, said flow control valve comprising,
        a body including at least two body sections, defining a lumen extending there through; and
        a septum interposedly positioned between the at least two body sections, the septum having an opening, the opening including a slit and at least two holes, wherein said septum at least substantially seals said lumen; and
        at least two posts coupled to at least one of the at least two body sections, a portion of said posts being disposed with a portion of said holes when the septum is in a closed position,
wherein rotation of at least one of said body sections in relation to said septum repositions said posts within said opening which results in the activation of said valve.

16. The medical device of claim 15, wherein the plane of rotation is substantially perpendicular to said lumen.

17. The medical device of claim 15, wherein said medical device is a vascular access device.

* * * * *